(12) United States Patent
Mitchell et al.

(10) Patent No.: US 9,814,437 B2
(45) Date of Patent: Nov. 14, 2017

(54) ANATOMIC RANGE PLANNING IN POSITRON EMISSION TOMOGRAPHY

(71) Applicant: Siemens Medical Solutions USA, Inc., Malvern, PA (US)

(72) Inventors: Matthew Mitchell, Knoxville, TN (US); Shiv Shanker Verma, Knoxville, TN (US); Collin Schaeffer, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 556 days.

(21) Appl. No.: 14/182,323

(22) Filed: Feb. 18, 2014

(65) Prior Publication Data

US 2015/0119703 A1 Apr. 30, 2015

Related U.S. Application Data

(60) Provisional application No. 61/894,927, filed on Oct. 24, 2013.

(51) Int. Cl.
*A61B 5/05* (2006.01)
*A61B 6/00* (2006.01)
(Continued)

(52) U.S. Cl.
CPC ............ *A61B 6/5294* (2013.01); *A61B 6/037* (2013.01); *A61B 6/545* (2013.01); *A61B 6/0407* (2013.01);
(Continued)

(58) Field of Classification Search
CPC ....... A61B 5/0555; A61B 5/055; A61B 6/032; A61B 6/463; A61B 6/037; A61B 6/5241
See application file for complete search history.

(56) References Cited

U.S. PATENT DOCUMENTS 6,490,476 B1 * 12/2002 Townsend ............. A61B 6/032
250/363.03
6,963,768 B2 * 11/2005 Ho .................... G01R 33/56375
600/415
(Continued)

OTHER PUBLICATIONS

Beyer, T., et al. "The Biograph: a premium dual-modality PET/CT tomograph for clinical oncology." Electromedica-Erlangen—69.2 (2001): 120-126.

*Primary Examiner* — Joel Lamprecht (57) ABSTRACT

Anatomic range planning is provided in positron emission tomography (PET). The user indicates one or more ranges on an image of a patient based on anatomy. Rather than planning by bed position, the planning is based on the anatomy of the patient without reference to the length of the PET detector. The user interface for PET examination avoids overlapping boxes and other confusion based on bed position. Different anatomical ranges may be assigned different PET parameters, such as reconstruction parameters. A processor may automatically alter the examination (e.g., by extending the detection range beyond the region of interest or by increasing duration at an end position) to account for the sensitivity profile since the anatomical region of interest is known. Anatomical region specific directions may be included as part of planning, aiding in performing different protocols for different anatomical ranges.

16 Claims, 6 Drawing Sheets

(51) Int. Cl.
*A61B 6/03* (2006.01)
*A61B 6/04* (2006.01)
(52) U.S. Cl.
CPC .......... *A61B 6/0457* (2013.01); *A61B 6/4258* (2013.01); *A61B 6/465* (2013.01)

(56) References Cited

U.S. PATENT DOCUMENTS

| | | | | |
|---|---|---|---|---|
| 7,103,233 B2* | 9/2006 | Stearns | ................. | G06T 7/0024 378/4 |
| 2010/0220909 A1* | 9/2010 | Thielemans | .......... | G06T 11/005 382/131 |

* cited by examiner

ANATOMIC RANGE PLANNING IN POSITRON EMISSION TOMOGRAPHY

RELATED APPLICATIONS

The present patent document claims the benefit of the filing date under 35 U.S.C. §119(e) of Provisional U.S. Patent Application Ser. No. 61/894,927, filed Oct. 24, 2013, which is hereby incorporated by reference.

BACKGROUND

The present embodiments relate to planning in nuclear medicine, such as positron emission tomography (PET). In particular, planning is provided for detecting from a volume of the patient that is longer than the field of view of the PET detector.

PET user interfaces support examination planning based on multiple integral bed positions. In this "stop and shoot" approach, different bed positions are dictated by the physical axial length of the PET detector. For example, the examination is divided into a plurality of bed positions spaced less than a length of the PET detector apart. The examination region for each bed position corresponds to the length or field of view of the PET detector. These bed positions are arranged to provide overlapping examination at different locations.

To define the region to scan of the patient, the user indicates the starting bed position. The amount of overlap may be defined as well. Since each bed position has a length based on the PET detector, the user defines the number of bed positions and overlaps to provide for examining a diagnostic region of interest of the patient. The user configures only the number of integral bed positions to define the overall extent of scan. The user can determine the location of one end of the overall scan range, but the other end location and the positions of the individual bed positions are determined based on the integral math of gantry axial field-of-view. The integral math may not match the anatomy of the patient with specific bed positions. The user cannot easily optimize and adapt the examination protocol to the specific needs of various organ imaging. As a consequence, most users do not attempt to optimize scanning protocols for the different bed positions.

Another problem with typical PET examinations is sensitivity. The sensitivity profile of the PET detector across the axial field of view is triangular or trapezoid shaped, which leads to lower sensitivity and lower signal-to-noise ratio at the end planes of a given bed position. Where multiple bed positions are used, the overall sensitivity profile is generally more consistent within the diagnostic region of interest, but has decreased sensitivity and signal-to-noise ratio at the extremes due to no overlapping bed positions. Users compensate for the lowered sensitivity and signal-to-noise ratio by manually planning to begin and end the examination in positions that are beyond the area of diagnostic interest. This further complicates planning for the bed positions and results in imaging of parts of the patient that are not diagnostically desired. Alternatively, the users accept the lowered sensitivity and signal-to-noise ratio at the end planes.

During operation of the PET detector after planning, the user and patient are presented with progress references in the form of beds "X" of "Y" and/or time remaining per bed or for the overall scan. The user or system may provide a general instruction to the patient prior to the beginning of the overall scan, or the user may attempt to manually provide the instruction based on the coarse progress information. Since general instructions have minimal benefit as not timely and improper timing may lead to a reduction in examination quality, the user typically chooses not to give patient instructions during the examination itself and does not attempt advanced techniques, such as breath-hold during whole body examinations.

BRIEF SUMMARY

By way of introduction, the preferred embodiments described below include methods, systems, and computer readable storage media for anatomic range planning in positron emission tomography (PET). The user indicates one or more ranges on an image of a patient based on anatomy. Rather than planning by bed position, the planning is based on the anatomy of the patient without reference to the length of the PET detector. The user interface for PET examination avoids overlapping boxes and other confusion based on bed position. Different anatomical ranges may be assigned different PET parameters, such as reconstruction parameters. A processor may automatically alter the examination (e.g., by extending the detection range beyond the region of interest or by increasing duration at an end position) to account for the sensitivity profile since the anatomical region of interest is known. Anatomical region specific instructions may be included as part of planning, aiding in performing different protocols for different anatomical ranges.

In a first aspect, a method is provided for anatomic range planning in positron emission tomography (PET). An image of a patient as positioned on a bed of a PET scanner is displayed. An indication on the image of an anatomical starting point and an anatomical stopping point of anatomy of the patient is received. The anatomical starting point and anatomical stopping point are different than a length of a detector of the PET scanner or an integral multiplier of the length. The PET scanner operates as a function of the anatomical starting and stopping points.

In a second aspect, a non-transitory computer readable storage medium has stored therein data representing instructions executable by a programmed processor for anatomic range planning in positron emission tomography (PET). The storage medium includes instructions for generating an user interface of a PET scanner indicating two or more ranges of patient anatomy, the ranges free of overlap with each other and at least two of the ranges being of different lengths, each of the lengths being other than a measure of a detector of the PET scanner, and receiving different PET parameters for at least one of the ranges as compared to another of the ranges.

In a third aspect, a system is provided for anatomic range planning in positron emission tomography (PET). An x-ray detector is positioned to receive x-rays from an x-ray emitter for generating an x-ray image of a patient. A bed positioned between the x-ray emitter and the x-ray detector and in a PET detector. The bed is moveable within the PET detector. A processor is configured to determine a speed of the bed for an end portion of an entire region of interest of the patient in the x-ray image and/or an extension of bed movement beyond the entire region of interest of the patient in the x-ray image. The processor is configured to determine as a function of sensitivity at the end portion.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Examination planning in nuclear medicine examinations is based on anatomy of the patient. Various aspects of the examination may benefit from an anatomy centric planning, such as region-by-region scanning configuration, region-by-region patient instructions, and automated entire region sensitivity planning. Any one or more of these aspects may be used.

In one aspect, a user interface and workflow are provided for anatomic range planning and variable protocols in nuclear medicine examinations. Using stop and shoot planning, there is no easy way to optimize the acquisition to the individual patient's anatomy. Rather than planning by bed position, a user interface for examination planning is based on an individual patient's anatomy with different requirements per organ. The user may place the scan range at any arbitrary position relative to a reference image of the patient's anatomy. Optimizations of the scan may be configured based on anatomic regions, such as high resolution imaging of the head-and-neck and motion management of the chest within a single scan of the patient.

In another aspect, a user interface for automatic compensation of noise variations due to geometric sensitivity in PET imaging is provided. The user interface allows the user to define the region of diagnostic interest based on patient anatomy, and the system automatically accounts for the lowered sensitivity and signal-to noise ratio in the end planes of this anatomic region. The system adds an additional scanning region to the ends of the scan range or increases the duration at the end planes, increasing sensitivity and signal-to-noise ratio in end regions of diagnostic interest.

In yet another aspect, a user interface and workflow for patient coaching is based on patient anatomy being scanned. The user interface allows automatic patient coaching based upon the anatomical region of the patient that is currently or about to-be scanned. For planning, the user may choose pre-recorded messages to be played audibly or visually to the patient prior, during, and/or after the system scans a specific anatomic region of the patient's body. Alternatively or additionally, the user interface may be configured to provide a visual indication to the user so that manual instructions to the patient may be given with proper timing based on scan progress relative to anatomy. The properly timed feedback may increase the likelihood of higher quality examinations. Properly timed instructions may also enable users to routinely perform advanced imaging techniques. Advanced imaging techniques, where the imaging quality is directly dependent upon the patient following special instructions at the proper time in the examination (e.g., breath-hold during a portion of a whole body examination), may more likely be successfully performed.

Figure 1:
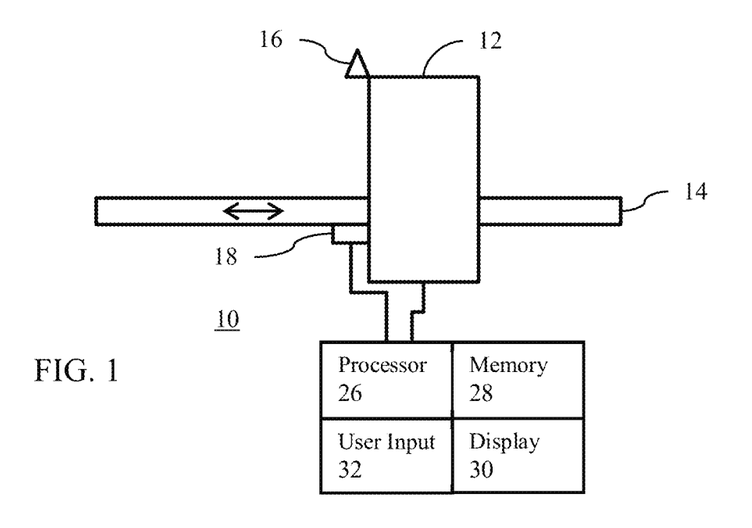
FIG. 1 is a block diagram of one embodiment of a system for anatomic range planning in PET.

FIG. 1 shows one embodiment of a system 10 for anatomic range planning in nuclear medicine, such as positron emission tomography (PET). The system 10 is part of a PET imaging system, but may be part of a single photon emission computed tomography (SPECT) system. The processor 26, memory 28, display 30, and user input 32 are part of a medical imaging system, such as the PET system 10. In other embodiments, the system 10 is a computer, server, workstation or other processing device that acquires PET data from a separate scanner and/or that plans for the acquisition of PET data with a separate scanner. The processor 26, memory 28, display 30, and/or user input 32 may be part of an archival and/or image processing system, such as associated with a medical records database workstation or server. In other embodiments, the processor 26, memory 28, display 30, and/or user interface 32 are a personal computer, such as desktop or laptop, a workstation, a server, a network, or combinations thereof. The processor 26 and memory 28 may be provided without other components for implementing the method.

The system 10 includes a PET detector 12, bed 14, x-ray emitter 16, x-ray detector 18, processor 26, memory 28, display 30, and user input 32. Additional, different or fewer components may be provided. For example, a network interface is provided. As another example, the x-ray emitter 16 and x-ray detector 18 are separate from the PET detector 12 and/or bed 14 or not provided. An optical camera or data created model or representation of the patient may be used instead of an x-ray image. Other imaging modalities may be used instead of x-ray.

In general, the memory 28 stores previously used, programmed, or other pre-determined plans and/or data used for generating and operating a user interface for planning. The display 30 displays the user interface to the user. The processor 26 controls configuration of the user interface, operation of the PET detector 12 and the bed 14, and/or reconstruction from data from the PET detector 12.

The system 10, using hardware, software, or hardware and software, interacts with a user for PET planning, controlling operation of the PET scanner, and/or generating a PET image. The system implements the method of FIG. 2 or another method to provide anatomic range planning in PET. The processor 26 or devices controlled by or connected with the processor 26 perform the acts of FIG. 2.

The PET detector 12 is a ring of sensors, forming a tube into which the bed 14 passes or is positioned. A source emits positrons. Any of different sources of emissions may be provided. For example, the positrons are emitted from a radioisotope. Any radioisotopes may be used. Different radioisotopes emit or result in photons having different energies that will exhibit different characteristics when interacting with a collimator of the PET detector 12. The radioisotope decays, resulting in either direct photon emission (SPECT) or positron interaction with electrons and subsequent photon emission (PET). In PET, photons are emitted in generally opposite directions due to the positron interaction. One or both of these photons are detected by the PET detector 12, depending on the point of origin, direction of travel, and position of the PET detector 12. Other sources of photons may be used in other embodiments.

A multi-channel collimator may be provided with the PET detector 12. The collimator is an array of apertures. For example, a honeycomb structure of lead septa or plates is provided. Other materials may be used. Each channel of the collimator is an aperture or bore through which photons may pass. Rather than a hexagon shape, the aperture of the bores may have any shape. The septa are thin to minimize blockage of the photons. The multi-channel collimator has a nominally uniform depth or height that is the same for each of the bores, but may vary from bore to bore due to manufacturing defects. Any or no multi-channel collimator may be used.

The multi-channel collimator is adjacent to the sensors of the PET detector 12. The collimator lies adjacent the sensors or between the sensors and the source. A gap may separate the collimator from the sensors. The collimator covers the entire array of sensors or only part of the array. The collimator is placed to cause photons emitted from sources to pass through one or more bores generally along a perpendicular line to the detector and not pass through at other angles, such as +/−5 degrees from 90 degrees. Photons traveling at a sufficiently large enough angle away from orthogonal are blocked from the sensors in order to enforce a geometrical relationship on the detected photons. Due to the bore aperture within the cylinder of the PET detector 12, photons traveling along lines over a range of angles may be accepted while photons traveling along ray lines at greater angles are blocked, defining a field of view of the PET detector 12.

The sensors are operable to detect emissions. The sensors are an array of photo multiplier tubes or silicon avalanche photodiodes. Crystals connected with the tubes or photodiodes convert the photons into light. The tubes or photodiodes detect the light. The location, energy, and/or timing of the detection are recorded or processed as a detected photon.

The x-ray emitter 16 and the x-ray detector 18 are connected with a housing of the PET detector 12. Alternatively, the x-ray emitter 16 and x-ray detector 18 are part of a separate system (e.g., computed tomography, fluoroscopy, or x-ray) sharing the bed 14 with the PET detector 12 or disconnected from the PET detector 12 and the bed 14.

The x-ray emitter 16 is positioned opposite the x-ray detector 18. The bed 14 and the patient on the bed 14 are between the x-ray emitter 16 and the x-ray detector 18. The emitter 16 and detector 18 may be moveable or fixed relative to the bed 18. A single scan may scan the entire or majority of the patient, or a sequence of scans are performed to scan the entire or majority of the patient. To scan, the x-ray emitter 16 emits x-rays, which pass through the patient, and the detector 18 detects the x-rays. The intensity of the detected x-rays indicates the density of the patient along the respective path of travel.

The detected x-rays are used for an image of the patient. An x-ray image is generated of the patient. For example, a topogram or projection through the patient from a fixed reference point above the patient is created.

The x-ray image shows internal and external anatomy. For example, bone and/or organs (e.g., heart, lungs, skull, brain, back-bone, hip, breast, ribs, and/or intestines) within the patient are represented in the image. The skin or outer portions of the patient, such as a boundary or edge of the patient from the x-ray viewing perspective, may also be represented. The arms, legs, head, neck, hips, chest, hands, feet, or other external anatomy may be represented. Filtering, segmentation, or other processes may be used to enhance particular anatomy.

In alternative embodiments, other modalities for representing external and/or internal portions of the patient may be used. For example, a camera is used to represent external anatomy. As another example, magnetic resonance is used to represent anatomy. The image may show only internal or only external anatomy.

The position of the x-ray emitter 16 and detector 18 relative to the bed and/or the PET detector 12 is known. Calibration, measurement, or fixed relationship may be used. The x-ray image of the patient indicates specific locations that may be used by the PET detector 12. Alignment between the patient and the x-ray detector 18 may be provided using laser location.

The bed 14 is a gurney, table, or other patient resting or support location. The bed 14 is robotic, such as providing for mechanical and automated movement of the patient through the bore of the PET detector 12. The bed 14 is positioned or positionable in the PET detector 12 bore and between the x-ray emitter 16 and x-ray detector 18. The bed 14 moves under control of the processor 26 to different positions for examining the patient with the PET detector 12 and/or creating the x-ray image. The tubular or laterally open examination subject bore of the PET detector 12 encloses a field of view in which the bed 14 and patient are positioned. The field of view for the x-ray imaging may overlap or be separate from the field of view for the PET detector 12. The bed 14 may position for both PET and x-ray at a same time or sequentially. The patient bed 14 may be moved into the examination bore in order to generate images of the patient.

In one embodiment, the bed 14 operates to move continuously through the bore. PET detection occurs while the bed 14 is moving. The speed of the bed 14 is constant or varies during this continuous bed motion examination. Alternatively, the bed 14 moves in increments to different bed positions in a stop and shoot approach. The bed 14 moves, stops, PET detection is performed, and then the bed moves to the next position to repeat PET detection.

The user input 32 is a keyboard, mouse, trackball, soft buttons, hard buttons, touch pad, touch screen, combinations thereof, user sensor, or other now known or later developed user input device. For example, the user input 32 is a combination of devices provided for interacting with a computer or imaging system. The user input 32 is used to receive input from the user for the user interface of the system 10, such as for planning.

The processor 26 is a general processor, central processing unit, control processor, graphics processor, digital signal processor, three-dimensional rendering processor, image processor, application specific integrated circuit, field programmable gate array, digital circuit, analog circuit, combinations thereof, or other now known or later developed device for generating a user interface, receiving input from a user, displaying an image, controlling the system 10, and/or performing the acts of FIG. 2. The processor 26 is a single device or multiple devices operating in serial, parallel, or separately. The processor 26 may be a main processor of a computer, such as a laptop or desktop computer, or may be a processor for handling some tasks in a larger system, such as being part of the PET scanner housing the PET detector 12. The processor 26 is configured by instructions, design, hardware, and/or software to perform the acts discussed herein.

The processor 26 is configured to display a user interface. The user interface includes an image of the patient and locations for entry of information. For example, a box, field, drop down menu, list, or other user input option is displayed. The processor 26 also receives input from entry into the user interface. Alternatively or additionally, the processor 26 displays information to the user for action by the user.

Figure 2:
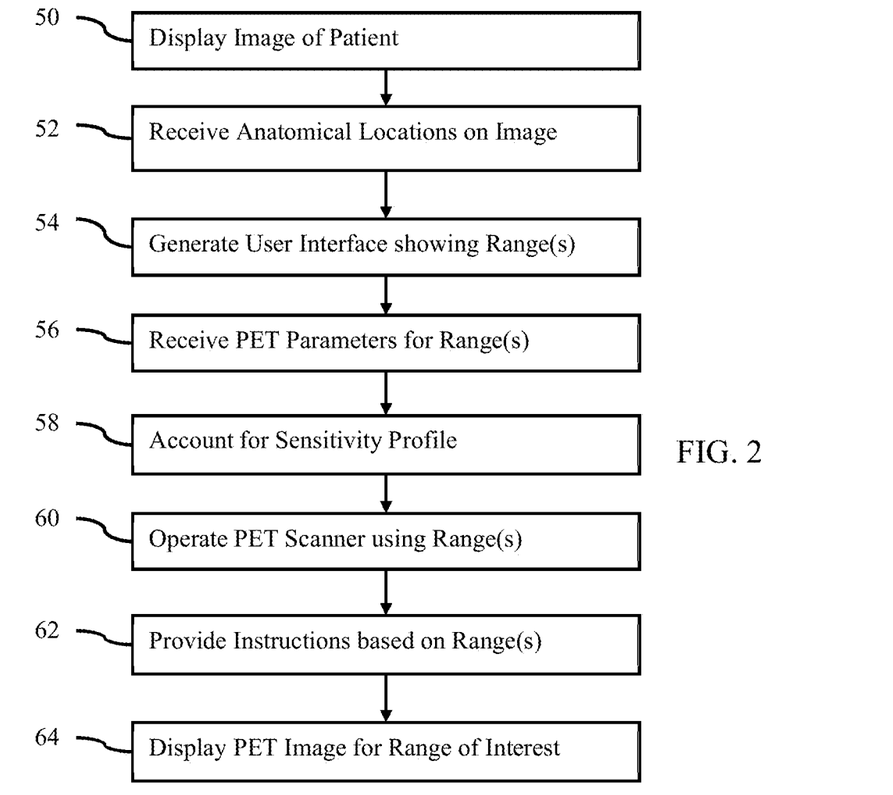
FIG. 2 is a flow chart diagram of an example embodiment of a method for anatomic range planning in PET.

The processor 26 is configured to perform the method of FIG. 2 or another method. The processor 26 performs the acts, controls other components (e.g., PET detector 12, bed 14, x-ray emitter 16, and/or x-ray detector 18), receives data from other components (e.g., PET data, bed position data, x-ray image data) to perform the acts, and/or acquires data to perform the acts of FIG. 2. For example, the processor 26 manages the user interface, controls PET detection or passes off information for control of PET detection, performs PET reconstruction or receives PET images, and displays PET and/or x-ray images. The processor 26 causes the display 30 to output the user interface.

The processor 26 is configured for planning with the user interface. The anatomy-based planning is provided by the processor 26. Three anatomy range-based features mentioned below for the processor are discussed further with respect to the method of FIG. 2.

The processor 26 allows for definition by the user of different, non-overlapping anatomical ranges and corresponding different PET parameters (e.g., protocols) for the ranges. Alternatively or additionally, the processor 26 allows for definition by the user and output, based on the definition, of instructions for the patient relative to anatomy.

For stop and shoot, the processor 26 calculates bed positions based on the user indications of anatomy rather than the user indication bed positions (e.g., rather than the user indicating the first position of the bed, the number of positions, and the amount of overlap). Alternatively, the processor 26 calculates the speed or duration of the bed for different anatomical regions in continuous bed motion detection.

In another alternative or additional embodiment, the processor 26 determines a speed of the bed 14 for an end portion of an entire region of interest of the patient and/or an extension of bed movement beyond the entire region of interest of the patient based on a user selected scan range relative to anatomy. The sensitivity profile of the PET detector 12 is used to account for sensitivity relative the user indication of a diagnostic region of interest of the patient in the image.

The memory 28 is a graphics processing memory, video random access memory, random access memory, system memory, cache memory, hard drive, optical media, magnetic media, flash drive, buffer, database, combinations thereof, or other now known or later developed memory device for storing data or video information. The memory 28 is part of the imaging system 10, part of a computer associated with the processor 26, part of a database, part of another system, a picture archival memory, or a standalone device.

The memory 28 stores anatomical range information, planning data, user interface inputs, user interface configuration, image information, reconstruction instructions, reconstruction data, and/or other information. The memory 28 or other memory is alternatively or additionally a non-transitory computer readable storage medium storing data representing instructions executable by the programmed processor 26 for anatomic range planning in PET. The instructions for implementing the processes, methods and/or techniques discussed herein are provided on non-transitory computer-readable storage media or memories, such as a cache, buffer, RAM, removable media, hard drive or other computer readable storage media. Non-transitory computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone, or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The display 30 is a monitor, CRT, LCD, plasma, projection, touch screen, printer, or other display for outputting a user interface. The display 30 is fed images from a buffer. The images include user interface information, such as the user interfaces represented in FIGS. 3 and 6.

FIG. 2 shows one embodiment of a method for anatomic range planning in PET or other nuclear medicine imaging. In general, user entry of anatomical positions of the patient is used for planning and/or operation of the PET examination. The user interface provides for anatomical-based selections without bed position limitations or without user entry of the number of bed positions, user entry of the overlap of bed positions, or the display of multiple bed positions. The user interface allows definition of exclusive or non-overlapping ranges of anatomical interest and leaves bed positioning and/or speed to the processor.

The method of FIG. 2 is performed by the medical system 10 of FIG. 1, the PET scanner, a computer, a processor, or a different system. For example, the medical system, an interface of the medical system, and/or a processor of the medical system allows definition of anatomical ranges for PET examination planning of different protocols by range, determines the range of examination to account for sensitivity, and/or determines a speed of bed motion to account for sensitivity. As another example, the PET scanner provides visual and/or audio instructions appropriate for a given anatomical range of the patient during the examination or when most appropriate.

The acts are performed in the order shown, but other orders may be provided. For example, act 54 is performed throughout the method, such as presenting a user interface without the ranges, with the ranges, with PET parameters for the ranges, with patient coaching information for the ranges, during operation of the PET scanner, when providing instructions, and/or when displaying PET images. Similarly, act 50 is performed as part of generating the user interface, so may be performed with, before, or after any of the various other acts.

Additional, different, or fewer acts may be provided. For example, acts for acquiring an image of the patient or other acts for PET examination are performed. As another example, acts for interacting with the user interface are provided. In yet another example, acts 56, 58, and/or 62 are used in any combination, such as alone, two of the acts, or all three of the acts (e.g., act 58 and/or 62 are not performed). As another example, act 64 is not performed.

In act 50, an image of a patient as positioned on a bed of a PET scanner is displayed. Alternatively, the image is of the patient at another location. Once positioned on the bed of the PET scanner, laser markers are used to align the image information with the patient and the patient with the PET scanner.

The display is on a screen of a workstation, computer, or other device used by a specialist, physician, or other for planning a PET examination. For example, the display of the image of the patient is generated as part of a user interface of the PET scanner.

The user interface is generated for planning, confirming a plan, examination of the patient, and/or display of results of PET examination. The medical system generates the user interface locally or remotely. Using software, hardware or both, the medical system causes display of graphics, images, or other screen outputs for user interaction. The user interface includes fields, check boxes, selectable buttons, selectable menus, tabs, or other software generated input devices for user interaction. Any navigation structure may be provided, such as including all information on one screen, including a hierarchal structure where one or more selections lead to other screens with appropriate or narrowed options. Tab structures may be used to configure different aspects or types of information with the user interface (e.g., tab for patient, tab for physician, and tab for scan).

Figure 3:
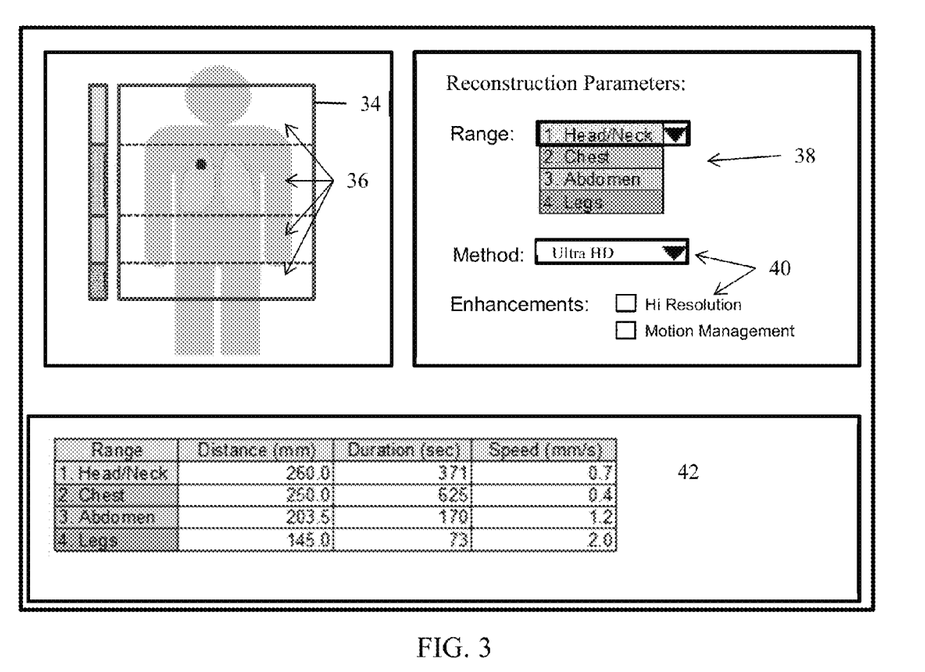
FIG. 3 illustrates a user interface for anatomical range planning in PET.

In one embodiment, the user interface is for configuring the medical system for operation. FIG. 3 shows an example user interface for PET examination. The configuration may be to scan a patient for imaging. The user interface is part of a workflow of the user for operating the medical system and/or for patient diagnosis. The medical system outputs, in the user interface, pre-determined workflow attributes, such as options relevant for the medical system and/or the patient. For example, options for scanning a patient are output as part of the user interface. The options are variables. For PET, the options may include a list of different imaging enhancements, different reconstruction types or options, or other PET parameters.

At any point in the process, such as in response to a user trigger, user selection, or automatically, the image of the patient is displayed on the user interface. The image is of part of the patient or the entire patient. In the example shown in FIG. 3, the entire patient is shown from head to toe. More than one image may be shown, such as images of different types, with different processing, and/or from different view angles. The image shows external and/or internal anatomy of the patient.

In one embodiment, the image is an x-ray-based topogram of the patient. The patient as positioned on the bed of the PET scanner is imaged from above. The x-ray emitter and x-ray detector connected with or part of the PET scanner image the patient. The x-ray image is looking down on the patient, but may be from any angle. X-ray images provide information on the density along paths of travel. As a result, the x-ray image represents both external anatomy (e.g., head, legs, chest, arms, neck, and abdomen) and internal anatomy. In the example of FIG. 3, the lungs and heart are represented in the graphic used to represent an actual x-ray image. In alternative embodiments, the image is an optical image, such as from a camera, an ultrasound image, a magnetic resonance image, or a PET image taken as a precursor to further examination.

In act 52, an indication of an anatomical starting point and an anatomical stopping point is received. The user uses the user input to indicate the range, line, point, or other anatomical locations. For example, the user drag and drops, clicks and drags, selects, slides, rotates, or otherwise interacts with a graphic (e.g., box, line, or other shape) on the image. The user may position boxes with or without overlap. The length or axial extent of each box may be changed or set by the user based on the anatomy of the patient. The user may place a line to define different ranges. As another example, the user is prompted to click or select one or more locations where a line is to be placed.

In alternative embodiments, a processor identifies specific anatomy and selects or indicates the anatomical locations. The processor selected locations may be displayed for user confirmation.

The indication is relative to anatomy of the patient. The image of the patient is of anatomy. Specific anatomy may be selected, such as indicating a range or axial extent of an organ or group of organs. For example, the anatomy is divided into head and neck, chest, abdomen, and leg ranges as represented in FIG. 3. Other anatomical specific indications may be used, such as selecting a range covering an organ (e.g., lungs). Depending on the reason for the PET examination, a location may be of increased interest. For example, a narrow chest region corresponding to a patient's breasts may be of particular interest for a whole-body examination performed due to a diagnosis of breast cancer. The breast region is indicated as one anatomical range. While shown as axial or length ranges, the range may be defined along one or more other dimensions.

The anatomical starting and stopping points define a range. For example, the user places boxes for four ranges 36 shown in FIG. 3. Additional, different, or fewer ranges may be provided. The user may place separator lines (e.g., dashed lines) or boxes to separate anatomical ranges or the entire region 34 of diagnostic interest into separate ranges 36. The separate ranges 36 do not overlap. A starting point may be the stopping point of a previously identified range. There is no parameter used to set the amount of overlap. The separate ranges 36 are defined relative to anatomy and are not necessarily based on the length of the PET detector or an integral multiplier of that length. The indications are disconnected from the PET detector dimensions or detection characteristics. The indications are arbitrary or may be anywhere along the patient rather than at fixed increments relative to the PET detector.

The starting and stopping points may be for any portion of the entire region 34 of interest. Each separate range 36 has a starting and stopping point. The entire region 34 of interest likewise has anatomical starting and stopping points. The user may position a box, position lines, or select points to define the entire region 34 of interest. As shown in the example of FIG. 3, the entire region 34 is for a whole body scan. Parts of the body may not be scanned even in a whole body scan, such as the feet and top of the head. In other embodiments, the entire region 34 is smaller, such as being just the chest and abdomen ranges 36, just the abdomen range 36, just the chest range 36, or other portion of the patient. Alternatively, the entire patient is the entire region 34.

Any order of indication may be used. For example, the entire region 34 is defined by sequentially indicating different ranges 36. As another example, the entire region 34 is indicated, and then portions of the entire region 34 are indicated to provide the separate ranges 36. In either approach, anatomic regions 36 of the patient may be defined within the overall scan range (e.g., entire region 34) to allow for different values for variables by anatomy in protocol optimization.

The indications are for anatomic regions correlated with patient anatomy. The indications are arbitrary relative to the PET detector or relative to bed positions, other than any physical limitations of the total range of bed motion. Depending on bed operation, any level of resolution in anatomical marking may be used, such as 2 mm. The anatomical starting point and anatomical stopping point for any range may be different than a length of a detector of the PET scanner or an integral multiplier of the length. A given anatomical range 34, 36 may be longer or shorter than the PET detector or an examination length of the PET detector at a given position. The anatomical starting and stopping points are provided without an indication of bed position, as anatomy is the determining factor rather than bed positions. User or processor input is of positions arbitrary relative to the PET scanner as the anatomical starting and stopping points are relative to the image of the patient and without PET field of view limitations.

In one embodiment, the user selects from a list of anatomical ranges or the processor provides initial separation. The user then indicates the locations each of the predetermined anatomical ranges. In other embodiments, the user indicates a range and then labels the range using any terminology or using names from a menu. Any amount of processor assistance and/or pre-determined or standardized ranges and/or range names may be used, including none.

In act 54, a user interface showing the ranges is generated. The user interface is generated as part of providing the indications, after completion of setting the indications, or at other times. The user interface is displayed for interaction with the user. As the user interacts with the user interface as part of a workflow for diagnosis, planning, and/or imaging, the user interface is updated. The user interface is generated or updated in response to user input of one or more of the anatomical ranges 34, 36 on the image of the patient. Each update may include all, some, or none of the previously received indications of the anatomical ranges.

The generated user interface includes the image of the patient with overlaid or adjacent indication of the ranges of the patient anatomy. For example, FIG. 3 shows color coded bars. Color coding may instead or additionally be provided as an overlay on the image. Brackets may be used to show the anatomical ranges 34, 36. Arrows may be used to show the ranges or separation of ranges 34, 36. Boxes (e.g., solid box for entire region 34), lines (e.g., dashed lines separating the entire region 34 into separate anatomical ranges 36), or pattern overlay may indicate the different ranges 34, 36. Any combination of these or other indications of separate portions or the entire region 34 may be used.

The ranges 36 indicated in the user interface are free of overlap with each other. Different ranges 36 have the same or different lengths. For example, FIG. 3 shows each of four anatomical ranges 36 having different lengths from all other of the anatomical ranges 36. The user interface displayed to the user is free of bed position indicators. The lengths of the ranges 36 are not a measure of the detector of the PET scanner, but are instead indications of anatomy.

In act 56, PET parameters are received for the examination of different portions of the patient. PET parameters are any setting for the PET examination. For example, different PET reconstruction parameters are received. Reconstruction parameters may include the protocol or method used for reconstruction, such as back projection, 3D iteration, point spread reconstruction, motion management reconstruction, high definition reconstruction, low definition reconstruction, or others. The reconstruction parameters may be values for variables used in reconstruction. The PET parameters may be for enhancements, such as a type of filter, filter setting, resolution, or motion compensation (e.g., breathing indicator or ECG synchronization). Any variable used in PET examination may be a PET parameter.

The parameters are received from user entry or processor selection. For example, FIG. 3 shows a portion 40 of the user interface for entering PET parameters. The user selects an anatomical range on the image, color bar, or in the range labels 38. Color coding may be used to relate the ranges 36 from the image to the ranges in the portion 40. The anatomic regions are color coded for easy reference when defining scan and reconstruction parameters elsewhere in the user interface. Symbols, patterns, sequence, or other relational approaches may be used. Relational information is not used in other embodiments.

Different PET parameters are provided for the different ranges 36. The user selects, inputs, or otherwise enters one or more PET parameters for each of the different ranges. For example, an ultra-high definition reconstruction is selected from a list in portion 40 for the selected head and neck region in portion 38. For the legs anatomical region, a faster, simpler, or lower resolution method for reconstruction may be selected. For the chest region, a motion compensated (e.g., motion management) enhancement or method may be selected. The processor determines values for variables based on the selected PET parameter.

Different PET parameters or values of the parameters are selected for the different regions. The PET examination may be optimized for speed, resolution, or other reason by anatomic region. One anatomic region may be emphasized over others or different approaches may be used to account for the differences in anatomy. For example, the legs may not require as much image detail for a given PET examination, so a reconstruction method associated with greater speed is used as compared to other regions. As another example, the PET examination for the chest is performed more rapidly (e.g., faster bed movement in the region in continuous bed motion scanning) to avoid a user with breathing problems having to hold their breath. Alternatively, motion management (e.g., breather or ECG trigger) and a slower PET examination time are provided for the chest region for the same reason. One or more anatomical regions may share some or all of the selected PET parameters. The selection is based on the reason for the PET examination and the anatomy, so may vary by patient, physician, application, region, time, or location.

Using the user interface, anatomic regions may be configured for different scan optimizations or enhancements based on the needs of the patient's anatomy located in each region. For example, reconstruction is defined based on the anatomic range. Reconstruction optimizations are determined by the unique needs of the different anatomic ranges 36. As another example, operations or processes in addition to the reconstruction method are selected or not as enhancements. These enhancements are determined by the unique needs of the different anatomic ranges 36.

For continuous bed motion, the user may input a different bed speed for different regions. This may result in more duration of the bed in a given anatomical region as compared to others. Alternatively, the selection of the reconstruction method and/or an enhancement results in different bed speeds for different regions. In other embodiments, the user does not indicate any bed speed, but the processor determines the bed speed based on the selected PET parameters.

Another portion of the user interface shows values determined by the processor in response to selections by the user in portions 38, 40, and of the ranges 34, 36. The table 42 shows speed, duration, and distance for each of the regions. In other embodiments, the user may enter values in the table 42, which are then reflected in the ranges 36 or parameter entry portions 38, 40. In alternative embodiments, the table 42, the enhancement selection, the reconstruction method, and/or color bar are not provided. Additional or different selection items or user interface components may be provided.

In act 58, the entire anatomical range 34 (e.g., starting and stopping points) is used to account for sensitivity of the PET detector. The PET detector has a sensitivity profile for a given position. The profile may be measured, assumed, or determined using calibration or type of PET detector. Over the entire range 34, the sensitivity profile may also or alternatively be determined. For the step and shoot approach, the sensitivity profile is based on the bed positions and the duration at each bed position. For continuous bed motion, the sensitivity profile is based on the speed or duration as the bed moves relative to the PET detector. In either approach, the sensitivity at the ends of the entire region 34 is lower than elsewhere, dropping off rapidly. Signal-to-noise ratio also drops at the ends of the range.

Figure 4:
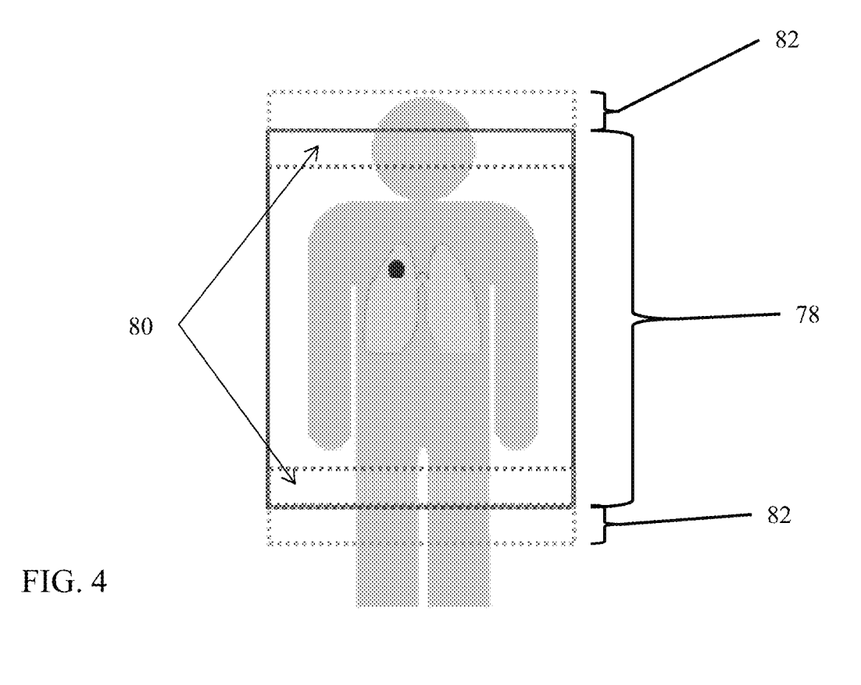
FIGS. 4 and 5 illustrate example approaches to account for the sensitivity of the PET detector in range planning.
Figure 5:
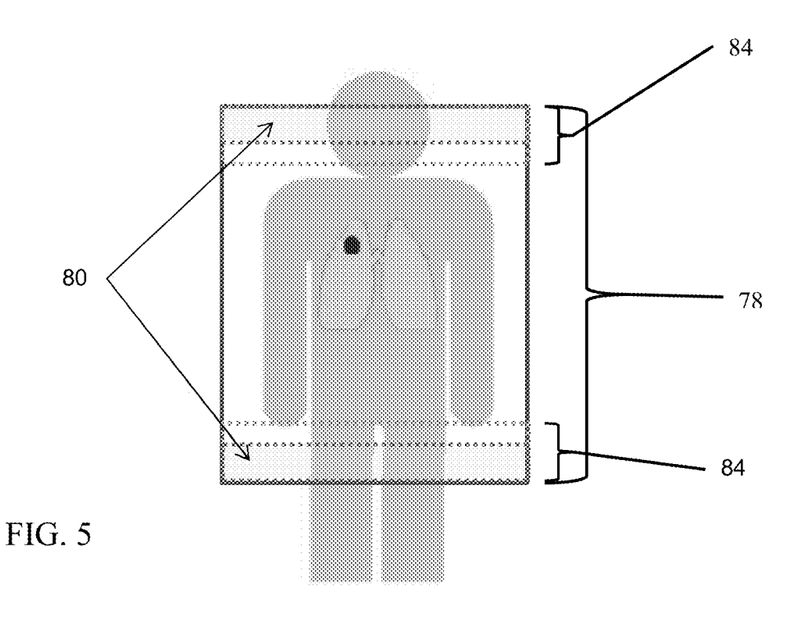

FIGS. 4 and 5 graphically represent the locations of reduced sensitivity. The entire region 78 is the anatomic locations for which diagnostic information is sought. Within that entire region 78, areas 80 are imaged areas or volumes with increased noise due to reduced sensitivity relative to the remainder of the imaging area or region 78. Without accounting for this sensitivity and signal-to-noise drop off, any PET images of the entire region 34 of diagnostic interest may have poor quality for locations within about ½ a detector length of the ends.

To account for the sensitivity drop off, the anatomical region 34 of interest is used. By indicating the region of interest based on anatomy, the locations for which good or sufficient quality imaging is sought are known. The processor may then adjust the actual examination to account for the decrease in sensitivity at one or both ends of the examination range. FIG. 4 represents one approach, adding to the extent or range of examination. FIG. 5 represents a different approach, increasing the duration of the examination near the ends. Only one of the two approaches is used for a given end, or both approaches may be used in combination for a given end. The sensitivity is increased by duration or extension at one or both ends of the entire anatomical region 34 of interest.

The processor receives the anatomical region 34 from the user interface. Using the sensitivity profile, the processor calculates the extension and/or duration to be used. The sensitivity profile is used to determine the magnitude of the extension and/or duration. For a given PET detector, the magnitude may be pre-determined, so is the same for any given examination. Different magnitudes for different situations may be provided, such as magnitude depending on the overall length of the anatomical region 34, the speed of bed motion due to the method selected for a given anatomical range 36 at the end, or other factor. From the user perspective, the anatomical region 78 is provided, and the processor handles the sensitivity part rather than requiring the user to position beds while considering sensitivity as well as anatomy.

FIG. 4 shows computed extensions 82. The anatomical range is expanded by the processor so that the locations of lower sensitivity and higher noise are moved entirely or partly out of the anatomical region 78 of interest for diagnosis. The additional region is used for examining the patient (e.g., detecting emissions). However, the additional region (i.e., extensions 82) may not be used for imaging. Instead, the addition results in more emission data being collected in the areas 80 of the anatomical region 78 of interest. The system automatically adjusts the beginning and end positions of the scan to optimize the sensitivity profile across the desired imaging area or region 78. The additional included scan area or extensions 82 may ensure image quality across entire desired imaging area or region 78.

FIG. 5 shows a computed increase in duration. The PET detector is maintained at or proceeds more slowly in an end region 84 of the anatomical region 78 of interest. The end region 84 corresponds to one length of the PET detector. The system adjusts the scan duration of the area equal to the axial length of the scanner field-of-view at the beginning and end of the desired imaging area or region 78. In alternative embodiments for continuous bed motion examination, the end region 84 may be greater or lesser length than the PET detector field of view. Within the end region 84, the bed moves more slowly and/or detects for a longer time than would otherwise occur given the examination settings. For example, the bed may be configured to move at one speed throughout an anatomical range that includes the end region. Due to the sensitivity, the bed moves at the configured speed for part of the anatomical range and moves more slowly at another part (i.e., the end region 84). Additional time is included in the scan area or region 78 to ensure image quality across the entire desired imaging area.

In act 60 of FIG. 2, the PET scanner operates as a function of the anatomical starting and stopping points. The user initiates the scan, such as activating in the user interface. The processor then controls the bed and/or PET scanner to examine the patient and/or generate a PET image.

The anatomical ranges are used for controlling operation of the PET scanner. Any operation of the PET scanner may be controlled using the anatomical information. For example, the speed and resulting duration (continuous bed motion) or just duration (step and shoot) within a given anatomical range is determined based on the selected PET parameters for the anatomical range. The duration and/or speed are different or the same for different anatomical ranges. The reconstruction for the different anatomical ranges is different or the same, depending on the settings (e.g., method and enhancements) selected for the anatomical ranges. Different reconstruction parameters are used for data from different anatomical ranges. Other PET scanning may be different due to the different settings.

The bed is controlled to provide the desired speed or duration. For continuous bed motion, the center or other location of the PET detector relative to the ends of the anatomical ranges is used to change from one speed to another. For step and shoot, the processor sets bed positions by anatomical range, avoiding overlap between ranges. During operation, the bed is positioned and stays at the assigned position for a given duration, providing equal distribution through each given anatomical range. A given bed position may be used in more than one range, such as an overlapping bed position set by the processor to avoid sensitivity reduction.

In one embodiment of operation of the PET scanner, the entire range of the PET scanning is extended. For example, an extra bed position or an extended region of continuous bed motion is added onto the region of interest. The bed is operated to provide for the extension in scanning. Emissions are detected over a greater extent of the patient than desired diagnostically. For continuous bed motion, emissions are detected while continuously moving the bed in extended areas. The entire movement range of the bed motion is based on the anatomical starting and stopping points plus the added extension for sensitivity. The system begins the scan by starting the field-of-view beyond the desired imaging area, and/or the system ends the scan by stopping the field-of-view beyond the desired imaging area.

In another embodiment, the bed is moved at different speeds in the respective anatomical ranges based on the sensitivity of the PET detector. At the ends of the entire region of interest, the bed is slowed or duration is increased. The system begins the scan by starting the field-of-view at the beginning edge of the desired imaging area, and/or the system ends the scan by stopping the field-of-view at the ending edge of the desired imaging area. At those beginning and ending locations as well as adjacent locations, the duration is increased to account of sensitivity.

Figure 6:
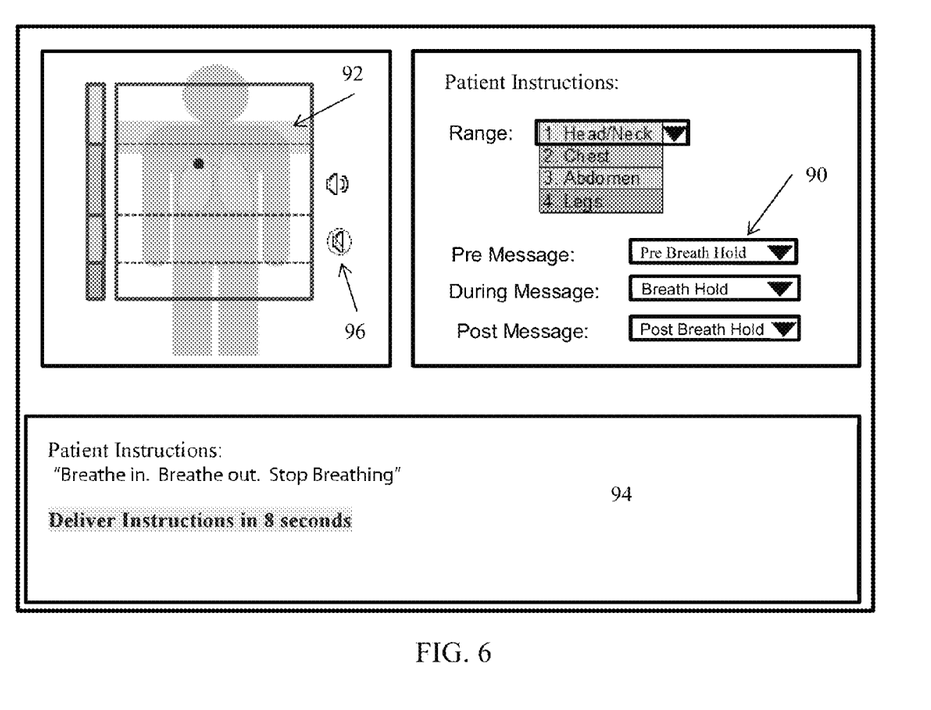
FIG. 6 illustrates a user interface for anatomical range planning of instructions in PET.

In act 62, patient instructions are provided based on the anatomical range. As the PET scanner operates, the bed is positioned relative to the PET detector for sensing from a field of view. The field of view of the PET detector changes. When the field of view is at, nearing, or leaving a particular anatomical range, instructions may be provided to the user and/or the patient. For example, when the center, a leading edge, or other part of the field of view contacts or begins to cover an end of an anatomical range 36, instructions are provided. In the example of FIG. 6, the field of view 92 is shown leaving a head region and beginning to acquire data for a chest region. Other trigger points may be used, such as when the field of view is within a predetermined or set distance of the anatomical range.

The instructions are anatomic region specific. Different instructions may be provided for different anatomical regions 36. One or more regions may not include instructions. When the first region to be examined is associated with instructions, the instructions are given before PET scanning and/or as the PET scanning starts. The instructions may be repeated or not repeated during the scan of that anatomical region. For subsequent anatomical regions, including intermediate and the last regions, the instructions are given after the PET scan or examination starts and before completion. The instructions may be given during, before, or after the scan of a given anatomical region. Some instructions occur after the start and before the end of PET scanning of a given protocol or workflow.

The instructions are for specific anatomical ranges. For example, the chest region may be examined. During examination of the chest region, the patient is instructed to hold their breath. Rather than instructing the patient to hold their breath at the beginning of a whole body examination, the instructions are provided at the relevant time, making it easier on the patient. Other instructions than breath hold may be provided. For example, the user is instructed where to position their arms. During scanning of an abdominal region, the arms may be positioned above the patient's head. During scanning of the legs, chest, and head region, the arms are positioned at the patient's side. Any anatomic region specific instructions may be provided. Other audio may vary by region, such as music being played or comforting statements or images.

The instructions are audio or video instructions. For example, a speaker of the PET scanner provides audio instructions. The audio instructions are a clause, command, or sentence. Alternatively or additionally, a beep or other sound or tone is made to indicate when to do something. As another example, the user interface or a display oriented for viewing by the patient displays text, symbols, animation, or other instructions indicating what the patient is to do. Both audio and video instructions may be provided.

The instruction is for the user, the patient, or the user and the patient. For example, the instruction indicates what the patient is to do. The instruction may be communicated to the patient, or the instruction may be communicated to the user for the user to pass on to the patient. FIG. 6 shows an example in the portion 94 of the user interface. The video instructions (e.g., "Breath in, breath out, stop breathing") are to the user on the user interface. Timing information is also given so that the user delivers the instructions at the desired time relative to the anatomy being scanned. In a further example, the PET scanner may play a recording with the same instructions. The user interface is used to show the user what instructions to expect. In alternative embodiments, the instructions are for the user to do something rather than the patient. For example, the user is instructed to move part of the patient, deliver a drug, or to shield themselves when an x-ray image is acquired during the PET examination.

The user may use the user interface to configure the PET scanner for providing the instructions. For example, selecting a reconstruction method for the chest region that does not include motion management (e.g., breathing belt triggering) may trigger automatic configuration to provide breath hold instructions. As another example, inputs for possible instructions are provided for user entry (e.g., menu or drop down list) during configuration of the examination. FIG. 6 shows input or selection of instructions in portion 90. No, one or more different instructions may be selected for each anatomical region. In the example of FIG. 6, three different instructions associated with different times during the scan of the chest region are provided. The messages may be targeted to specific times within the scan of the appropriate anatomic region.

The configuration occurs as part of any workflow. For example, the user selects a region to configure the instructions. As another example, the user is working on configuring for a given anatomical region and is provided with instruction configuration options. The portion 90 of the user interface is provided with appropriate fields or options for selecting instructions. The user selects the instructions or enters instructions. For example, the user selects from a drop down list populated with pre-determined instructions appropriate for a given anatomical region and/or PET parameters for that region. As another example, the user types in words to be read or the instructions to be given. The patient's name may be included so the instructions are more acceptable or polite.

An option for enabling or disabling instructions may be provided. For example, the user selects instructions or not for a given selected anatomical region using the buttons 96. The selection is made for each region. A default of no instructions or some generic instructions may be provided.

During operation of the PET scanner, the instructions are provided based on the configuration in the planning. The region being scanned or the field of view relative to the patient may be indicated on the user interface during operation (e.g., show the field of view 92 moving along or relative to the patient). Instructions corresponding to that region or the next anatomical region may be displayed or communicated to the user or patient. The instructions may include information as to when the instructions are to be carried out, such as telling the patient to hold their breath in five seconds or telling the patient to keep holding for ten more seconds during a breath hold.

In act 64, PET images are displayed. Using the reconstruction or reconstructions, the detected emissions for a volume are provided. A planar or volume (e.g., three-dimensional imaging) image may be generated from the detected emissions. Separate PET images for the separate regions may be provided. One PET image from data of different anatomical regions may be generated. Different portions of the image may be responsive to different amounts of PET data, different reconstruction, different bed speeds, or other differences. Any PET imaging may be used.

The PET image is of part or the entire region 34 of interest. Data from locations outside the anatomical region 34 of interest is not used for imaging. For example, data from the extensions 82 of FIG. 4 is not used. The extension provides for the field of view to dwell on the end portion of the region 34 of interest longer, providing greater sensitivity for that portion. The region 34 of interest is an anatomical region that the physician wants scanned. The extension is a mechanism for better quality imaging of the region 34 of interest, so is not part of the region 34 of interest that is imaged. In alternative embodiments, data from outside the region 34 of interest is included in the image.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for anatomic range planning in positron emission tomography (PET), the method comprising:
    displaying an image of a patient as positioned on a bed of a PET scanner;
    receiving a selection on the image, the selection identifying locations specific to an anatomical starting point and an anatomical stopping point of anatomy of the patient represented in the image, the anatomical starting point and anatomical stopping point being different than a length of a detector of the PET scanner and being different than an integral multiplier of the length; and then
    operating the PET scanner as a function of the anatomical starting and stopping points based on the selection.

2. The method of claim 1 wherein displaying the image comprises displaying an x-ray based topogram of the patient, the topogram including the anatomy comprising internal anatomical structure of the patient.

3. The method of claim 2 wherein displaying comprises generating the image of the patient with an x-ray emitter and x-ray detector connected with the PET scanner.

4. The method of claim 1 wherein displaying comprises displaying on a display of the PET scanner, and wherein receiving comprises receiving on a user input of the PET scanner.

5. The method of claim 1 wherein receiving comprises receiving the anatomical starting and stopping points without an indication of bed position.

6. The method of claim 1 wherein receiving comprises receiving the anatomical starting and stopping points as a first range and receiving indications of a second range, the first range, second range, and any other ranges not overlapping and disconnected from the length of the detector.

7. The method of claim 1 wherein receiving comprises receiving the anatomical starting and stopping points as an entire range of interest of patient and further receiving at least one division of the entire detection range into at least two portions free of overlap, each portion being defined based on the anatomy of the patient.

8. The method of claim 7 further comprising receiving different PET reconstruction parameters for two of the portions; and
    wherein operating comprises reconstructing data for the different portions using the respective different reconstruction parameters.

9. The method of claim 7 further comprising receiving different speed of movement of the bed for two of the portions; and
    wherein operating comprises moving the bed at the different speeds in the respective portions.

10. The method of claim 1 wherein receiving comprises receiving user input of positions arbitrary relative to the PET scanner as the anatomical starting and stopping points relative to the image.

11. The method of claim 1 wherein receiving comprises receiving the anatomical starting and stopping points as an entire range of interest of patient; and
    further comprising:
    computing, by a processor, a speed, an additional region, or speed and additional region for detection by the PET scanner at ends of the range of interest; and
    displaying PET images only for the range of interest of the patient.

12. The method of claim 11 wherein computing comprises computing an extension of the range of interest as the additional region, the extension computed as a function of a sensitivity profile of the PET scanner.

13. The method of claim 11 wherein computing comprises computing the speed at one of the ends as a function of a sensitivity profile of the PET scanner.

14. The method of claim 11 wherein receiving comprises receiving the anatomical starting and stopping points as a first range and receiving indications of a second range; and
    further comprising providing patient instructions relative to the second range during scanning with the bed approaching or in the second range.

15. The method of claim 14 wherein providing comprises providing audio instructions to the patient after a start of the scanning and before an end of the scanning of the patient.

16. The method of claim 1 wherein operating the PET scanner comprises detecting emissions while continuously moving the bed, an entire movement range of the bed being based on the anatomical starting and stopping points.

* * * * *